United States Patent [19]
Remon et al.

[11] Patent Number: 6,010,719
[45] Date of Patent: Jan. 4, 2000

[54] FREEZE-DRIED DISINTEGRATING TABLETS

[75] Inventors: Jean Paul Remon, Melle; Sam Corveleyn, Kruishoutem, both of Belgium

[73] Assignee: Universiteit Gent, Gent, Belgium

[21] Appl. No.: 08/931,257

[22] Filed: Sep. 16, 1997

[51] Int. Cl.$^7$ ........................................................ A61K 9/20

[52] U.S. Cl. .......................... 424/464; 424/435; 424/439; 424/440; 424/441; 424/465; 424/488; 514/772.3; 514/777; 514/778; 514/781; 514/782; 514/786; 514/948

[58] Field of Search .................................... 424/464, 465, 424/439, 441, 440, 488, 435

[56] References Cited

U.S. PATENT DOCUMENTS

| | | | |
|---|---|---|---|
| 4,495,177 | 1/1985 | Taracatac et al. | 424/147 |
| 5,785,989 | 7/1998 | Stanley et al. | 424/440 |

*Primary Examiner*—Thurman K. Page
*Assistant Examiner*—James M. Spear
*Attorney, Agent, or Firm*—Sughrue, Mion, Zinn, MacPeak & Seas, PLLC

[57] ABSTRACT

Freeze-dried disintegrating tablets, said tablets containing at least a therapeutic agent, a matrix forming agent and a binding agent, in which the tablets contain more than 20% by weight of a matrix forming agent selected from the group consisting of maltodextrins having a DE value between 12 and 40, isomalt and mixtures thereof, the weight ratio between said matrix forming agent and the binding agent being comprised between 2:1 and 50:1.

29 Claims, 4 Drawing Sheets

FREEZE-DRIED DISINTEGRATING TABLETS

FIELD OF THE INVENTION

The invention relates to freeze-dried disintegrating tablets, said tablets containing at least a therapeutic agent, a matrix forming agent and a binding agent.

THE PRIOR ART

Most pharmaceutical dosage forms for oral administration are formulated to be swallowed or chewed in order to deliver the drug. Pediatric and geriatric patients may have difficulties swallowing or chewing these tablets. Tablets that rapidly dissolve upon contact with saliva in the buccal cavity could present a solution to those problems and so there is an increased interest in fast dissolving dosage forms for buccal, sublingual and oral administration. Oral lyophilised products combine the properties of freeze-dried dosage forms, such as fast reconstitution, good preservation and stability, with the benefits of liquid dosage forms for bioavailability. Fast dissolving dosage forms are known in the art and described in U.S. Pat. No. 4,371,516; WO 94/14422; WO 95/01782 and U.S. Pat. No 4,946,684. The dosage form in U.S. Pat. No. 4,371,516 is described as providing a shaped article carrying a chemical or pharmaceutical agent, the article being able to disintegrate rapidly in the mouth. The shaped article comprises an open matrix of carrier material, carrying the active ingredients. This open matrix may be prepared by freeze-drying a composition comprising the active ingredient and the carrier material in solution. The carrier material described is gelatine which has been partially hydrolysed. The U.S. Pat. No. 4,946,684 discloses that other carrier materials may be used for example polysaccharides such as hydrolysed dextran, dextrin and alginates or mixtures with each other or with other carrier materials such as polyvinylalcohol, polyvinylpyrrolidone or acacia. U.S. Pat. No. 5,188,825 discloses a freeze-dried dosage form prepared from a solution including a bulk forming agent and a therapeutic agent containing ion exchange resins having a particle size less than 90 micron. The bulk forming agent may be gelatine or Xanthan gum.

WO 94/14422 describes the formulation of a rapidly disintegrating tablet including a partially collapsed matrix network that has been vacuum dried above the collapse temperature of the matrix.

WO 92/01782 discloses an improved technique for preparing a rapidly dispersing tablet by adding Xanthan gum to a liquid admixture of solvent, carrier components and a granular agent. The Xanthan gum facilitates suspension of the granular therapeutic agent in the liquid admixture, without affecting the dispersion qualities and texture of the tablet in the patients mouth.

Solid state emulsion refers to a dispersion of an immiscible oil phase within a solid phase and can be prepared using sucrose and mineral oil. Due to the presence of an oil phase, active ingredients can be dissolved in the oil, eliminating the need for a cosolvent. Different techniques have been described to prepare solid state emulsions including spray drying, solvent evaporation and freeze-drying. Dry emulsions prepared by spray drying an oil in water emulsion, containing lactose and maltodextrin in the aqueous phase and griseofulivin as model drug were evaluated as potential drug delivery. Freeze-drying of an oil in water emulsion can be an alternative method for the production of dry emulsions. The characteristics of a dry emulsion containing griseofulvin prepared by lyophilization using mannitol as the solid support were reported. Lyophilised dry emulsion tablets, using maltodextrins as amorphous cryoprotectant and solid support could be an interesting dosage form for the delivery of poorly soluble drugs. The oral bioavailability of vancomycin solid state emulsions each and vitamin E acetate redispersible dry emulsion has been reported. Eur. Patent No. 0159237 discloses a method for preparing a porous galenic form by lyophilization of an oil-in-water emulsion containing at least one pharmaceutically active ingredient. The aqueous phase comprises a substance selected from the group of organic fillers (eg. Milk powder, mannitol, the maltodextrins), thickening agents (eg. Natural gums, synthetic gums and cellulose derivatives) and their admixtures. The present invention discloses an improved formulation for the preparation of rapidly disintegrating tablets of a therapeutic agent. The invention is related to the use of maltodextrins with a DE value (dextrose equivalent) between 12 and 40 or isomalt in combination with a binding agent, preferably a thickening agent, in the formulation of solutions, suspensions and emulsions which are frozen and dried in alveolar packs in order to obtain rapidly disintegrating tablets. The tablets can be obtained by freeze-drying a solution of maltodextrins having a DE value between 12 and 40 or isomalt or a combination thereof in combination with one or more thickening agents such as the cellulose derivatives (eg. hydroxyethylcellulose, hydroxypropylmethylcellulose, methylcellulose) or Xanthan gum. The therapeutic agent can be dissolved or suspended in this solution prior to lyophilization. The tablets can also be obtained by freeze-drying an oil-in-water emulsion, where the water phase consists of the solution described above and the active ingredient is dissolved in the oil phase.

BRIEF DESCRIPTION OF THE INVENTION

The invention relates to a freeze-dried disintegrating tablets, said tablets containing at least a therapeutic agent, a matrix forming agent and a binding agent, in which the tablets contain more than 20% by weight of a matrix forming agent selected from the group consisting of maltodextrins having a DE value between 12 and 40, isomalt and mixtures thereof, the weight ratio between said matrix forming agent and the binding agent being comprised between 2:1 and 50:1, in which said matrix following agent and the binding agent are present in the tablets in an amount for ensuring a strength of the tablets of at least 1.5N and a disintegration time of the tablets between 10 and 120 seconds, said strength being the maximal force recorded when penetrating at a speed of 0.1 mm/second a cone probe over a depth of 1 mm in a tablet.

When using as matrix forming agent a maltodextrin with a DE value of 10, the freeze-dried tablets had a disintegration time greater than 120 seconds, while when using maltodextrin with a DE value of 50, it was possible to obtain tablets with a strength of at least of 1.5N and a disintegration time of less than 120 seconds. However, such tablets containing maltodextrin with a DE of 50 were unstable. It has now been found that by selecting specific matrix forming agent and by using the appropriate amount of said specific matrix forming agent as well as the appropriate amount of binding agent, it was possible to obtain stable freeze-dried tablets having a strength of the tablets of at least 1.5N and a disintegration time of the tablets between 10 and 120 seconds.

Preferably, the binding agent is selected from the group consisting of water soluble thickening agents, such as Xanthan gum, methylcellulose, hydroxypropylmethylcellulose, hydroxyethylcellulose and mixtures thereof.

According to specific embodiments of tablets of the invention, the tablets contain:

at least a co-solvent for the therapeutic agent, for example from 0.1% to 5% by weight of at least a co-solvent for the therapeutic agent, such as a polyethyleneglycol with a molecular weight lower than 10,000, propyleneglycol, glycerol, the presence of said solvent increasing the release rate of the therapeutic agent, and/or at least a surfactant, for example polysorbates, lecithin's, polyethoxylated castor oil, N-octenyl-succinate starch, sucroesters and mixture thereof, the presence of said surfaciant increasing the solubility or the dispersion of the therapeutic agent, and/or an oil, such as a medium chain triglyceride, soya-bean oil, cotton oil, sesame oil, peanut oil and mixtures thereof, the presence of said oil improving the solubility or dispersion of the therapeutic agent, and/or an additive selected in the group consisting of sweetening agents, carboxylic acid, citric acid, ascorbic acid and mixtures thereof, and/or an antioxidant selected from the group consisting of EDTA, ascorbic acid, sulfites, bisulfites and citric acid.

Advantageously, said matrix forming agent and the binding agent are present in the tablets in an amount for ensuring a porosity of the tablets formed by pores having a mean pore diameter between 10 $\mu$m and 15 $\mu$m.

According to a preferred embodiment, the tablets have the form of substantially round lozenge with a diameter between 5 and 12 mm.

The invention relates also to method for the preparation of a freeze-dried disintegrating tablets according to the invention containing at least a therapeutic agent, a matrix forming agent and a binding agent, in which a liquid medium containing at least:

(a) a compound which is liquid at a temperature higher than 0° C., which freezes at a temperature lower than 0° C., and which is sublimed at temperature lower than 0° C. and at pressure lower than 100 Pa or about 1 mbar;

(b) a therapeutic active agent;

(c) a matrix forming agent at least partly soluble in said compound; and (d) a binding agent, is prepared, frozen and dried, the drying been carried out at a pressure lower than 100 Pa, preferably lower than 50 Pa, in which the liquid medium contains from 10 to 200 grams/liter of a matrix forming agent selected from the group consisting of maltodextrins having a DE value between 12 and 40, isomalt (mixture of 50% α-D-glucopyranosido-1,6-mannitol and 50% α-D-glucopyranosido-1,6-sorbitol) and mixtures thereof, the weight ratio between said matrix forming agent and the binding agent being comprised between 2:1 and 50:1, in which said matrix forming agent and the binding agent are present in the liquid medium in an amount for ensuring after freeze-drying of the liquid medium the preparation of tablets having a strength of at least 1.5N and a disintegration time between 10 and 120 seconds, said strength being the maximal force recorded when penetrating at a speed of 0.1 mm/second a cone probe over a depth of 1 mm in a tablet.

Advantageously, the liquid medium prepared is selected from the group consisting of solutions in which at least the matrix forming agent and the binding agent are dissolved, oil emulsion in which the matrix forming agent is dissolved, suspensions of the therapeutic agent in which at least the matrix forming agent is dissolved.

Preferably, the liquid medium is dried in at least two steps, a first drying step being carried out at a temperature lower than the freezing temperature of the liquid medium at a pressure lower than 100 Pa, while the second step is carried out at a temperature higher than the freezing temperature of the liquid medium at a pressure lower than 100 Pa.

According to a preferred embodiment of the method of the invention, the liquid medium contains from 1 to 30 grams/liter of a binding agent selected from the group consisting of water soluble thickening agents, such as Xanthan gum, methylcellulose, hydroxypropylmethylcellulose, hydroxyethylcellulose and mixtures thereof.

According to specific embodiment of the method, various product(s) are added to the liquid medium (which is preferably an aqueous medium). Such products are for example a solvent for the therapeutic agent, a solvent for the therapeutic agent, said solvent having a boiling point higher than the drying temperature of the liquid medium at said low pressure, a surfactant such as propyleneglycol, polysorbates, lecithins, polyethoxylated castor oil, glycerol, N-octenyl-succinate starch, sucroesters and mixture thereof, an oil such as a medium chain triglyceride, soya-bean oil, cotton oil, sesame oil, peanut oil and mixtures thereof and an additive selected in the group consisting of sweetening agents, C1–C4 carboxylic acid and mixtures thereof.

Advantageously, said matrix forming agent and the binding agent are present in the liquid medium in an amount for ensuring a porosity of the tablets formed by pores having a mean pore diameter between 10 $\mu$m and 15 $\mu$m.

The liquid medium before being frozen is advantageously poured in substantially round blisters with a diameter between 5 and 12 mm, so as to have a better control of the strength of the tablets obtained after drying.

DESCRIPTION OF THE INVENTION AND EXAMPLES

Detailed Description of the Invention

The invention relates to the formulation and production of rapidly disintegrating tablets by freezing and drying or by freeze-drying of a solution, a suspension or an oil-in-water emulsion. The invention is particularly useful for paediatric or geriatric patients that may have difficulties swallowing or chewing conventional tablets. The liquid admixture is filled into alveolar packs and placed on the shelves of a freeze-dryer. The liquid admixture is frozen and then subjected to sublimation to produce a solid tablet.

The general requirements for preparing a freeze-dried tablet are well known in the art. In this invention, the production of rapidly disintegrating tablets is described by freeze-drying either a solution, a suspension or an emulsion.

When a solution is freeze dried, the solution used to prepare the rapidly disintegrating tablets of this invention comprises advantageously a solvent, a matrix forming agent, a binding agent and a therapeutic agent. The matrix forming agent, the binding agent and the therapeutic agent are soluble or dispersible in the solvent. Deionized water is preferred as solvent, which can be frozen and sublimed. Matrix forming agent means the excipient which provides the solid matrix support for the tablet after the solvent is sublimed. The matrix forming agent used is selected in the group consisting of maltodextrins having a DE value between 12 and 40, isomalt and mixtures thereof. Maltodextrins having a DE value between 12 and 40 have a good water solubility and a high glass transition temperature, whereby a fast disintegration of the freeze-dried tablets can be reached (less than 120 seconds) while a high glass transition temperature is an important parameter both for the lyophilization process and the formulation. During primary drying (the first drying step), drying temperatures above Tg' (glass transition temperature of the frozen product) result in a loss of the microstructure formed during the freezing process. With low DE maltodextrins (eg. DE14 having a Tg'-12,09° C.) in freeze drying formulations, higher product temperatures can be used during primary drying. Higher product temperatures result in shorter cycle times, because of an increase in sublimation rate. The glass transition temperature of the freeze-dried material (Tg) is an important formulation parameter: it gives the maximal safe storage temperature of the formulation. The high Tg value of formulations with low DE maltodextrins can be an additional advantage of the use of these excipients in freeze-dried tablets. Isomalt or palatinit is $\alpha$-D-glucopyranosido-1,6-mannitol and $\alpha$-D-glycopyranosido-1,6-sorbitol 1:1. When using isomalt as matrix forming agent, tablets have improved mechanical strength. The matrix forming agents can be used in a concentration range between 1–20% w/v in the solution (i.e. 10–200 g/liter). Suitable binding agents are the cellulose derivatives (eg. hydroxyethylcellulose, hydroxypropylmethylcellulose, methylcellulose) or Xanthan gum (i.e. thickening agents). These binding agents are advantageously used in a concentration range between 0.1 and 3% w/v (i.e. from 1 to 30 g/liter). The therapeutic agent is preferably dissolved in the liquid admixture prior to freeze-drying. It is possible to include a cosolvent or surfactant or a combination into the solution in order to increase the solubility of the pharmaceutically active ingredient. Suitable cosolvents or surfactants are polysorbates, esters of sorbitan, polyethyleneglycols, propyleneglycol, glycerol, N-octenyl-succinate starch, sucrose esters. These cosolvents or surfactants are for example used in the concentration range 0.001–3% w/v (i.e. from 0.01 g to 30 g/liter).

In case a suspension is freeze dried the suspension used to prepare the rapidly disintegrating tablets is similar to a solution as described above. But where the therapeutic agent is suspended in this solution, prior to freeze-drying, the binding agent or thickening agent increases the viscosity of the suspension and is suitable for preventing sedimentation of the solid drug particles. Said drug particles have for example a particle size lower than 350 $\mu$m.

An oil in water emulsion can also be used to prepare the freeze-dried tablets of this invention. Such an emulsion comprises for example an aqueous phase, a emulsifier-tablet binder and an oil phase. The aqueous phase consists of a solution of a matrix forming agent, said agent being maltodextrins having a DE value between 12 and 40, isomalt or a combination thereof. Palatinit or isomalt is a mixture 50% $\alpha$-D-glucopyranosido-1,6-mannitol and 50% $\alpha$-D-glucopyranoside-1,6-sorbitol. The matrix forming agents can be used in a concentration range between 1–20% w/v (10–200 g/liter). Suitable emulsifier-binding agents are the cellulose derivatives (eg. hydroxyethylcellulose, hydroxypropylmethylcellulose, methylcellulose) or Xanthan gum. These binding agents can be used in a concentration range between 0.1 and 3% w/v (1–30 g/liter). The oil phase of the emulsion may consist of a synthetic oil (e.g. medium chain triglycerides or oleic acid esters), a vegetative oil (e.g. soya-bean oil, cotton oil, sesame oil, peanut oil, . . .) and their mixtures.

The ratio water phase/oil phase of the emulsions can be 60–90% (w/w) water phase and 10–40% (W:W) oil phase. If necessary, the oil phase may contain one or several surfactants or cosolvents in order to increase the solubility of the pharmaceutically active agent in the oil phase. Possible surfactants or cosolvents are: polysorbates (Tween), esters of sorbitan (Span), polyethyleneglycols, polyethoxylated castor oil, lecithins, sucrose esters, N-octenyl-succinate starches.

Other substances may be incorporated in the solution, suspension or emulsion, said substances being for example sweetening agents, taste modifying agents and flavouring agents. Sweetening agents can be selected from the following: saccharose, glucose, acesulfame-K, cyclamates, aspartame, xylose and the saccharinates. Taste modifying agents are for example citric acid and ascorbic acid. These acids are also useful for increasing the stability of the tablets. These substances can be used in the concentration range 0.001–3% w/v (i.e. from 0.01–30 g/liter). The emulsion, solution or suspension is then filled in blisters made for example of PVC or polypropylene or others and these are placed on the shelves of a freeze-dryer and freeze-dried or lyophilised. Lyophilization is terminated by venting the drying chamber with air or a suitable gas such as nitrogen. The resulting tablets are characterised using scanning electron microscopy, porosimetric analysis, tablet strength testing, in vivo disintegration time, moisture analysis and in vitro dissolution testing.

Because of the plastic deformation it was impossible to test the hardness of the tablets on a conventional hardness tester and the strength of the tablets was determined with a texture analyser. For said measurement, the tablet was placed on a support and deformed in a defined, controlled manner by a cone penetration probe (length 4 cm, diameter of the base 2 mm) over a constant distance of 1 mm using a speed of 0.1 mm/s. A force (N) vs distance (mm) diagram was recorded. The maximal force (N) recorded when penetrating the cone probe over a depth of 1 mm in the tablet is a measurement of the strength of the tablet. For the determination of the in vivo disintegration time, each subject was given a coded sample and instructed to place the tablet under the tongue. The time required for complete disintegration of the tablet was recorded. The tablets were analysed on their residual moisture content after lyophilization using a Karl Fischer titration. The instrument was calibrated using disodium tartrate and water as a standard. Each tablet was pulverised, inserted in the titration vessel and analysed after a stirring time of 3 min. Dissolution testing was performed on lyophilised tablets containing 50 mg hydrochlorothiazide (HCT) in destined water at 37° C. using the paddle method (USP XXII) at a rotational speed of 100 rpm (Vankel VK7000 dissolution testing station, VanKel International, Homchurch, UK). Samples of 5 ml were withdrawn at regular time intervals, replaced by fresh medium by automatic sampling (Vankel VK8000 dissolution sampling station) and spectrophotometrically analysed at 273=m (Perkin Elmer Lambda 12 spectrophotometer, PE, Brussels, Belgium). The invention will be better understood by the following examples.

EXAMPLE 1

An aqueous solution was prepared by adding to 1 l deionized water, 62,50 g hydrochlorothiazide (HCT), 5 g Xanthan gum and maltodextrin (DE 24) at a rate of 50, 100 or 200 g.

After placing said solutions in round blisters of 0.8 ml (with a diameter of 15 mm) and after lyophilisation, tablets were obtained.

The lyophilisation was carried out according to the following protocol:

| Phase | Temperature | Time | Pressure |
|---|---|---|---|
| Freezing | −40° C. | 2 hrs | 1000 mbar |
| Primary drying | −10° C. | 12 hrs | 0.1 mbar |
| Secondary drying | 20° C. | 10 hrs | 0.01 mbar |

The following table 1 gives the composition of the tablets (on a dry matter basis):

|  | Maltodextrin | HCT | Xanthan Gum |
|---|---|---|---|
| Tablet 1 | 40 mg | 50 mg | 4 mg |
| Tablet 2 | 80 mg | 50 mg | 4 mg |
| Tablet 3 | 160 mg | 50 mg | 4 mg |

The tablets 1 to 3 were characterised on strength, disintegration time, porosity and residual moisture.

Results are shown in table 2:

|  | Disintegration time(s) | Strength (N) | Residual moisture (%) | Pore diameter ($\mu$m) |
|---|---|---|---|---|
| Tablet 1 | 32 | 0.53 | 6.23 | 15.8 |
| Tablet 2 | 31 | 1.31 | 6.31 | 12.3 |
| Tablet 3 | 47 | 2.88 | 5.63 | 8.8 |

Figure 1:
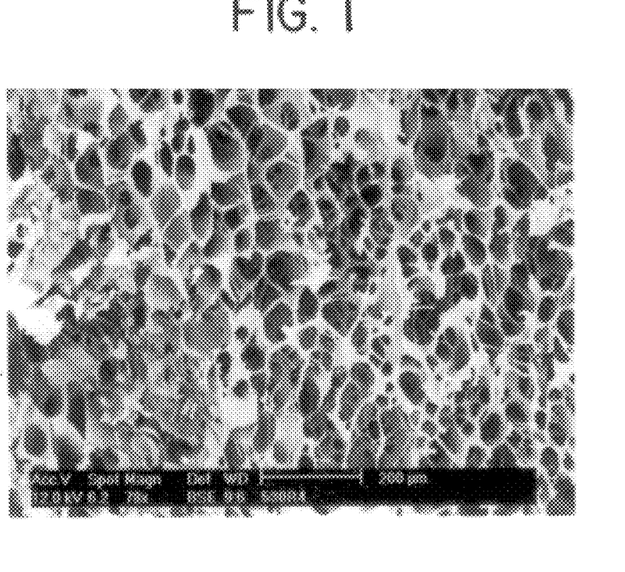
FIGS. 1 and 2 are scanning electron micrographs of the fracture plane of tablets containing maltodextrin with a DE of 24 and Xanthan gum.
Figure 2:
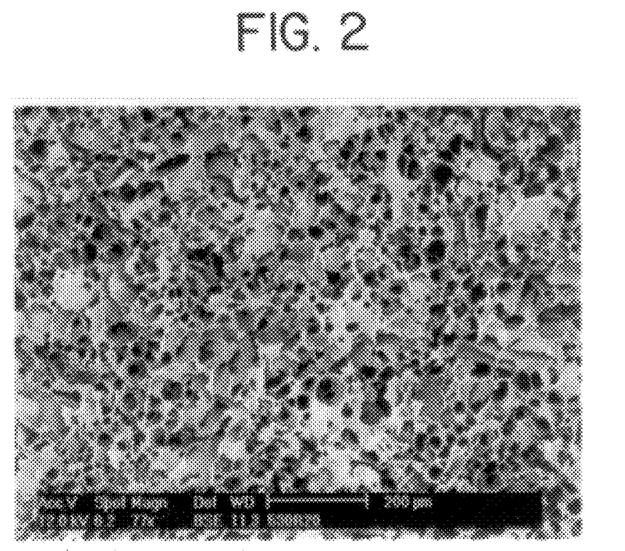

Scanning electron micrographs of the fracture plane of tablets 2 and 3 are shown in FIG. 1 and 2, respectively.

EXAMPLE 2

In said example, aqueous solutions containing 100 g/l maltodextrin DE 38, 62.5 g/l HCT and Xanthan gum at a rate of 1, 2.5, 5 and 10 g/l were prepared. Said solutions were filled in round blisters of 0.8 ml respectively with a length of 10 mm and with a length of 15 mm.

The composition (on a dry matter basis) of the tablets is given in the following table 3:

| Tablets | Diameter | HCT mg | Maltodextrin mg | Xanthan gum mg |
|---|---|---|---|---|
| 4 | 10 | 50 | 80 | 0.8 |
| 5 | 15 | 50 | 80 | 0.8 |
| 6 | 10 | 50 | 80 | 2 |
| 7 | 15 | 50 | 80 | 2 |
| 8 | 10 | 50 | 80 | 4 |
| 9 | 15 | 50 | 80 | 4 |
| 10 | 10 | 50 | 80 | 8 |
| 11 | 15 | 50 | 80 | 8 |

Figure 3:
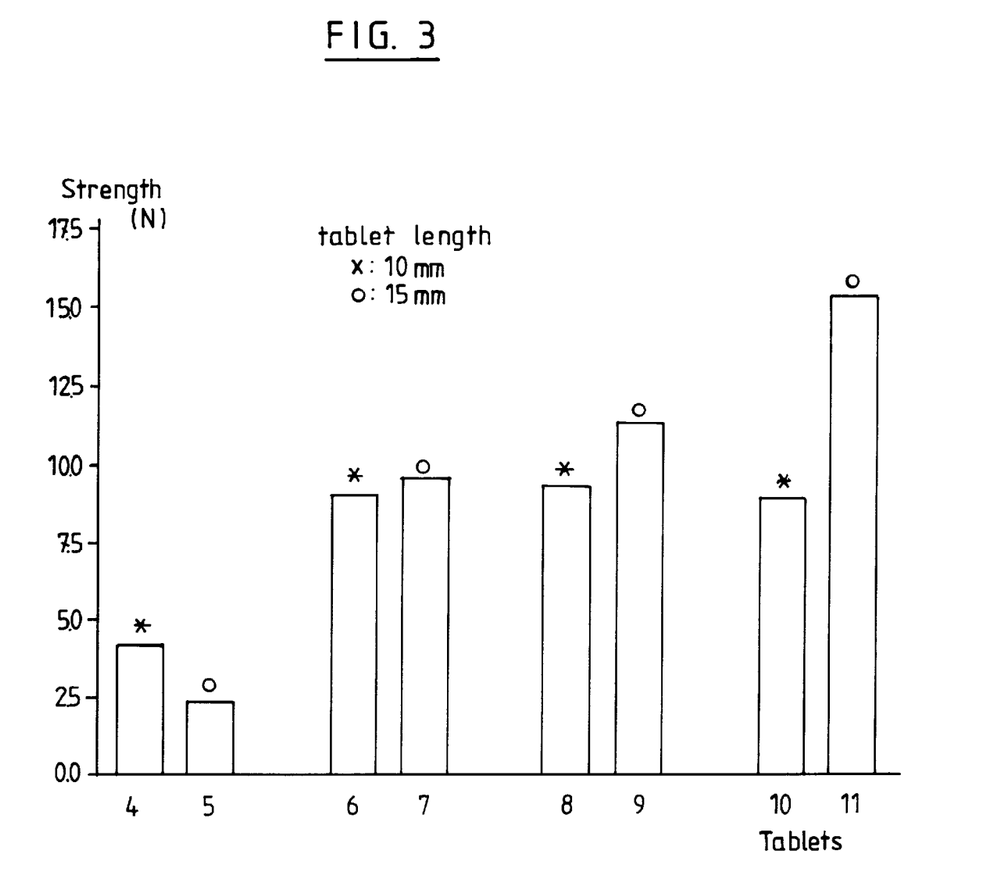
FIG. 3 is a graph showing the strength of tablets with a length of 10 mm (*) and with a length of 15 mm (°), said tablets containing maltodextrin with a DE of 38 and different amounts of Xanthan gum.

The strength of said tablets was measured and was given in FIG. 3.

As it can be seen from said FIG. 3, a high tablet strength could be reached when using more than 2.5 g Xanthan gum per liter.

Moreover, when using more than 5 g Xanthan gum/liter, the viscosity of the solution was increased up to 466 mPas, (Haake RV1, 25° C., rotor MV1). Such an increase of viscosity is important when sedimentation of drug solid particles has to be prevented.

As it can also be seen from FIG. 3, the tablets 6, 8 and 10 having a length of 10 mm have substantially the same strength.

It seems that when using tablets with a length of 10 mm, and at least 2.5 g/l of Xanthan gum, an error on the Xanthan gum concentration in the solution will have no impact on the strength of the tablets.

EXAMPLE 3

Tablets were prepared by using the following solution:

| Solution | | Composition mg (dry matter) after lyophilization in 0.8 ml blister |
|---|---|---|
| Maltodextrin DE 38 | 4 g | 160 |
| Xanthan gum | 0.1 g | 4 |
| Hydrochlorothiazide | 1.25 g | 50 |
| Deionized water | to 20 ml | |

Figure 4:
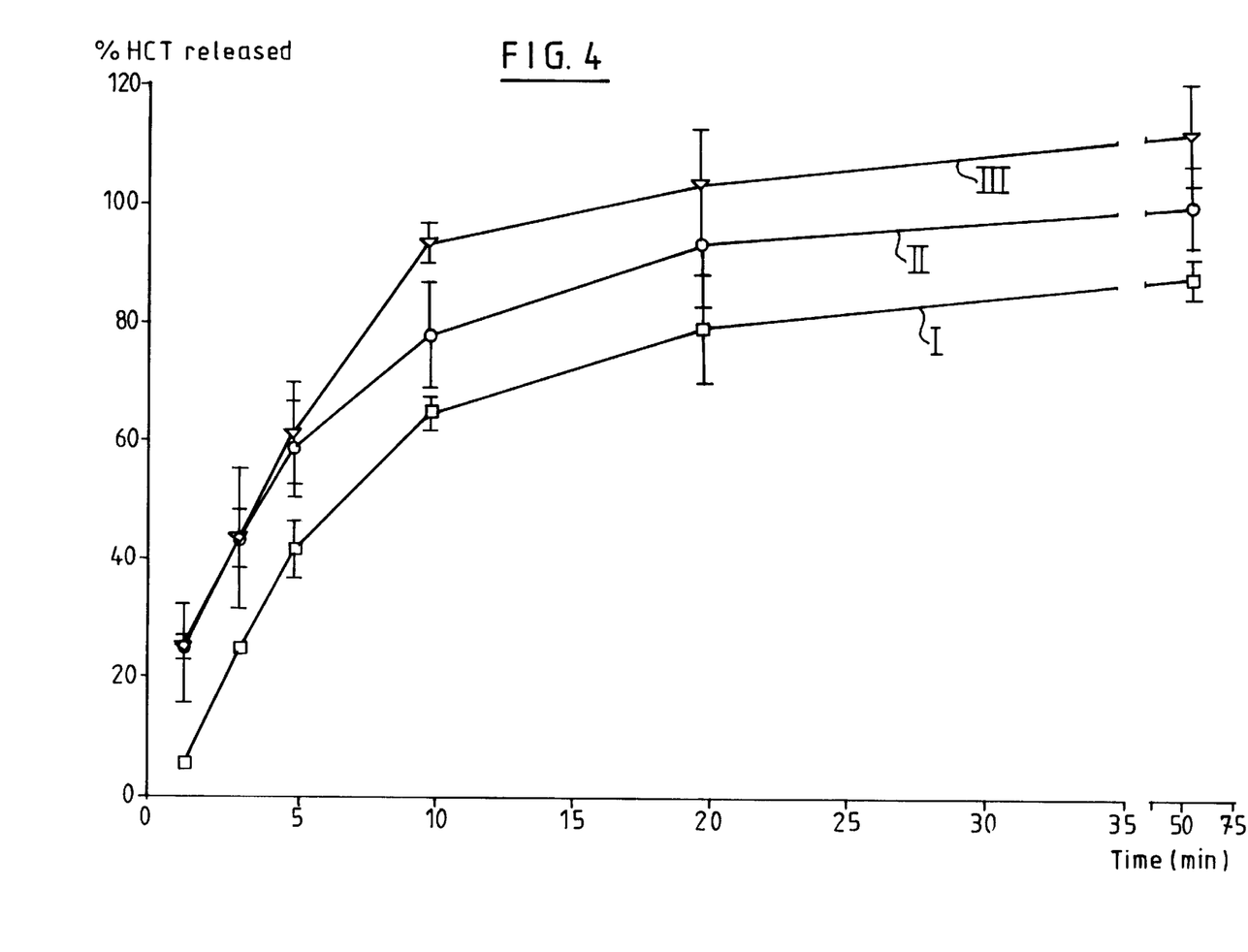
FIG. 4 is a graph showing the dissolution profile of tablets containing 50 mg of hydrochlorothiazide, tablets I being the reference tablets, tablets II containing 160 mg maltodextrin with a DE of 38 and 4 mg of Xanthan gum and tablets III containing 160 mg maltodextrin with a DE of 38, 4 mg of Xanthan gum and 8 mg of polyethyleneglycol (6,000).

The in vitro dissolution profiles of a conventional reference tablet and the lyophilised formulations are shown in FIG. 4. The % HCT released within 10 min was 64.55 ±2.87% and 77.84±8.94% for the reference tablets (Tablet I) and the lyophilised tablet (Tablet II) formulation, respectively.

EXAMPLE 4

Tablets were prepared by using the following solution:

| Solution | | Theoretical composition mg (dry matter) after lyophilization in 0.8 ml blister |
|---|---|---|
| Maltodextrin DE 38 | 4 g | 160 |
| Xanthan gum | 0.1 g | 4 |
| PEG 6000 | 0.2 g | 8 |
| Hydrochlorothiazide | 1.25 g | 50 |
| Deionized water | to 20 ml | |

The effect of the addition of 1% PEG 6000 (w/v) to the formulation on the dissolution profile was investigated. The addition of PEG 6000 (1% w/v) resulted in an increase of HCT release 93.3% was released from the lyophilised tablets (Tablet III) within 10 min (see FIG. 4).

EXAMPLE 5

The following solution was prepared for the formation of tablets:

| Solution | | Composition mg (dry matter) after lyophilization |
|---|---|---|
| Maltodextrin DE 38 | 40 g | 160 |
| Hydroxyethylcellulose | 2 g | 8 |
| Na₂EDTA | 20 g | 0.08 |
| apomorphin.HCl | 750 mg | 3 |
| Deionized water | to 200 ml | |

Apomorphine, a very potent mixed dopaminergic agonist when given subcutaneously is an effective agent in the treatment of "off" phases in Parkinsonian patients with motor fluctuations. However, the methods of administration currently used are expensive, technically complex and responsible for local side effects at the site of injection. As sublingual administration might be more appropriate for the patient, rapidly disintegrating tablets containing apormorphine could be very useful in the treatment of these "off" periods.

EXAMPLE 6

Aqueous emulsions have been prepared by using a Silverson mixer according to a standardised production protocol. The emulsifier-tablet binder is dispersed in the water phase, next the oil is added and the emulsion is mixed with the Silverson mixer.

Emulsions which were prepared had the following composition:

| Emulsion | Water (g) | Maltodextrin (g) | DE | HCT (g) | Miglyol 812 (g) | Methyl cellulose (g) |
|---|---|---|---|---|---|---|
| 1 | 74 | 4 | 38 | 6.25 | 20 | 2 |
| 2 | 70 | 8 | 38 | 6.25 | 20 | 2 |
| 3 | 74 | 4 | 24 | 6.25 | 20 | 2 |
| 4 | 70 | 8 | 24 | 6.25 | 20 | 2 |
| 5 | 74 | 4 | 12 | 6.25 | 20 | 2 |

The tablets formed by means of said emulsions had a diameter of 10 mm and contained 50 mg HCT, 160 mg Miglyol, 16 mg methylcellulose and 31 or 62 mg maltodextrin.

Said tablets have been analysed. The results of said analysis is given here after:

| Emulsion | Disintegration time (min) | Strength (N) | Residual moisture (%) |
|---|---|---|---|
| 5 | 1.8 | 1.4 | 1.88 |
| 3 | 1.0 | 1.6 | 1.93 |
| 4 | 4.0 | 2.7 | 1.95 |
| 1 | 0.8 | 1.6 | 1.85 |
| 2 | 2.4 | 3.0 | 2.5 |

Figure 5:
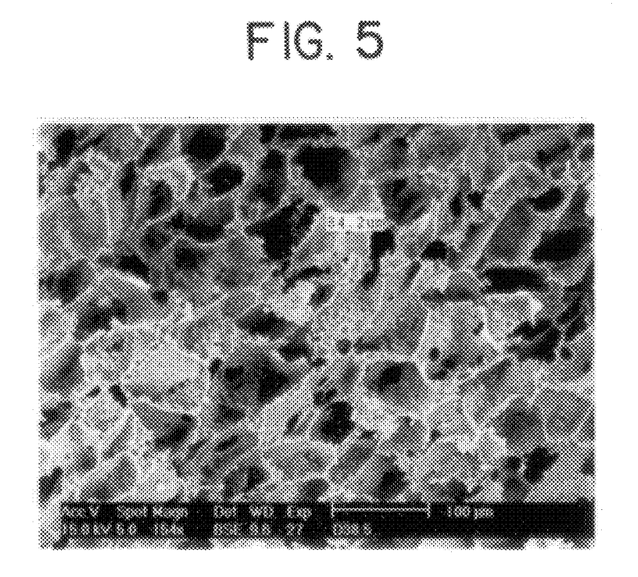
FIGS. 5 and 6 are scanning electron micrographs of the fracture plane of a tablet containing an emulsifier, methylcellulose and maltodextrin with a DE of 38.
Figure 6:
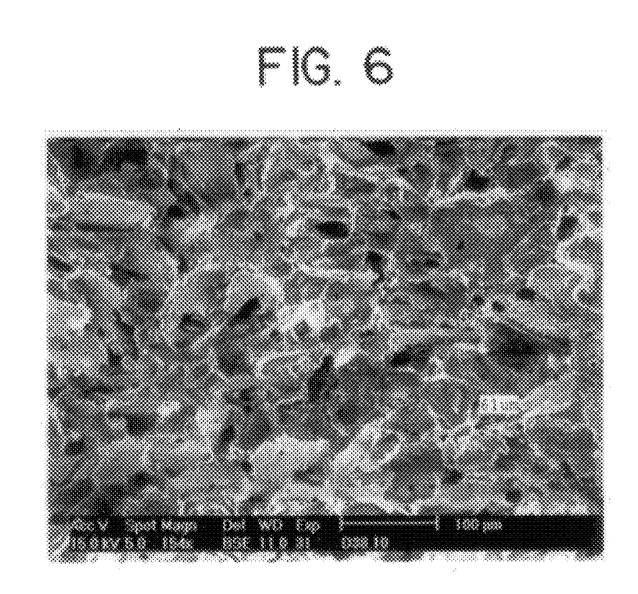

Miglyol 812 is a synthetic oil : a medium chain triglyceride. FIG. 5 and 6 are scanning electron micrographs of the fracture plane of tablets obtained from emulsion 1 and 2 respectively.

EXAMPLE 7

Emulsions have been prepared as explained in example 6.

The composition of the emulsions prepared as well of the 10 mm tablets obtained are given in the following tables:

| Emulsion | Water | Maltodextrin DE 38 | Miglyol | HCT | HPMC | Methylcellulose Low Viscosity | Methylcellulose High Viscosity |
|---|---|---|---|---|---|---|---|
| 6 | 70 g | 8 g | 20 g | 6.25 g | 2 g | | |
| 7 | 70 g | 8 g | 20 g | 6.25 g | | 2 g | |
| 8 | 70 g | 8 g | 20 g | 6.25 g | | | 2 g |

Methylcellulose Low Viscosity: viscosity of 15 mPas at 20° C. (2% aqueous solution)
High Viscosity : viscosity of 100 mPas at 20° C. (2% aqueous solution)

| Tablet composition (length 10 mm) Dry matter basis | | | | | | |
|---|---|---|---|---|---|---|
| Emulsion | HCT mg | Maltodextrin mg | Miglyol mg | HPMC mg | Methylcellulose Low mg | Methylcellulose Viscosity High mg |
| 6 | 50 | 21 | 160 | 16 | | |
| 7 | 50 | 64 | 160 | | 16 | |
| 8 | 50 | 64 | 160 | | | 16 |

The tablets have been analysed. The results of said analysis are given in the following table:

| Emulsion | Disintegration time (min) | Strength (N) | Residual moisture (%) |
|---|---|---|---|
| 7 | 0.9 | 2.85 | 2.15 |
| 6 | 1.2 | 3.05 | 1.65 |
| 8 | 1.3 | 2.74 | 1.99 |

The choice between methylcellulose and hydroxypropylmethylcellulose had no significant effect on tablet disintegration time, strength and residual moisture but was a factor influencing the viscosity of the emulsion prior to freeze-drying.

EXAMPLE 8

Emulsions have been prepared as in example 6.

The composition of the emulsions is given in the following table:

| Emulsion | Water (g) | Maltodextrin DE 38 (g) | HCT (g) | Miglyol (g) | Xanthan gum (g) |
|---|---|---|---|---|---|
| 9 | 70 | 8 | 6.25 | 20 | 0.25 |
| 10 | 70 | 8 | 6.25 | 20 | 0.5 |
| 11 | 70 | 8 | 6.25 | 20 | 1 |

Tablets have been prepared by lyophilising said emulsion. The dry content of the tablet (15 mm diameter) is given in the following table:

| Emulsion | HCT mg | Maltodextrin DE 38 mg | Miglyol mg | Xanthan gum mg |
|---|---|---|---|---|
| 9 | 50 | 64 | 160 | 2 |
| 10 | 50 | 64 | 160 | 4 |
| 11 | 50 | 64 | 160 | 8 |

The strength of the tablets containing Xanthan gum as a binder was significantly lower compared to the cellulose derivative containing tablets:

| Emulsion | Disintegration time(min) | Strength (N) | Residual moisture(%) |
|---|---|---|---|
| 9 | 1.11 | 0.62 | 2.52 |
| 10 | 1.71 | 0.82 | 2.41 |
| 11 | 2.46 | 0.78 | 2.85 |

EXAMPLE 9

An emulsion and tablets have been prepared as in example 6. The composition of the emulsion and tablets are given in the following table:

| | Emulsion | Tablet composition (mg) on dry matter |
|---|---|---|
| Isomalt | 8 g | 64 |
| Water | 70 g | |
| Soya-bean oil | 20 g | 160 |
| Lecithin | 0.6 g | 6 |
| Methylcellulose | 2 g | 16 |
| Cyclosporin A | 2.5 g | 20 |

Cyclosporin is a potent immunosuppressive agent which prolongs allograft survival in organ transplantation. Due to its lipophilic nature, the currently manufactured cyclosporin formulations (oral and soft gelatine capsules) use oil-and-alcohol solutions of the drug. The mean absolute bioavailability of these formulations is about 30% and shows a high inter and intra-individual variability. Lyophilised dry emulsion tablets, containing oil and lecithin to solubilise the drug, can be an alternative solid dosage form for the delivery of cyclosporin.

EXAMPLE 10

Emulsions and tablets have been prepared as in example 6.

The composition of the emulsions and tablets are given in the following tables:

| Emulsion | Water (g) | Isomalt (g) | HCT (g) | Miglyol (g) | Methylcellulose xx (g) |
|---|---|---|---|---|---|
| 13 | 70 | 8 | 6.25 | 20 | 1 |
| 14 | 70 | 8 | 6.25 | 20 | 2 |

Low viscosity methylcellulose.

| | Tablets composition mg | | Dry matter | |
|---|---|---|---|---|
| Emulsion | Isomalt | HCT | Miglyol | Methylcellulose |
| 13 | 64 | 50 | 160 | 8 |
| 14 | 64 | 50 | 160 | 16 |

The effect of emulsifier/binder concentration on isomalt containing lyophilised tablet characteristics is shown in the following table:

| Emulsion | Disintegration time(min) | Strength (N) | Residual moisture(%) |
|---|---|---|---|
| 13 | 0.51 | 0.5 | 1.2 |
| 14 | 1.35 | 1.5 | 1.5 |

The therapeutic agent or active agent is for example an agent selected in the group consisting of active agent is selected from the group consisting of hydrochlorothiazide, acetazolamide, acetylsalicylic acid, allopurinol, alprenolol, amiloride, antiarrhythmic, antibiotic, antidiabetic, antiepileptic, anticoagulants, antimycotic, atenolol, bendroflumethiazide, benzbromarone, benzthiazide, betamethasone, ester thereof, bronchodilator, buphenine, bupranolol, chemotherapeutic, chloridiazepoxide, chloroquine, chlorothiazide, chlorpromazine, chlortalidone, clenbuterol, clomipramine, clonidine, co-dergocrine, cortisone, ester thereof, dexamethasone, ester thereof, dextropropoxyphene, diazepam, diazoxide, diclofenac, diclofenamide, digitalisglycoside, dihydralazine, dihydroergotamine, diltiazem, iron salt, ergotamine, ethacrynic acid, ethinylestradiol, ethoxozolamide, fenoterol, fludrocortisone, ester thereof, fluphenazine, furorosemide, gallopamil, guanethidine, hormone, hydrochlorothiazide, hydrocortisone, ester thereof, hydroflumethiazide, immunosuppressive agents, ibuprofen, imipramine, indomethacine, coronartherapeutic, levodopa, salt of lithium, salt of magnesium, medroxyprogesteron acetate, menadione, methaqualone, 8-methoxypsoralen, methylcloothiazide, methyldopa, methylprednisolone, methyltestosterone, methylthiouracil, methylxanthine, metipranolol, molsidomin, morphine, naproxen, nicergoline, nifedipine, norfenefrine, oxyphenbutazone, papaverine, parmathasone, ester thereof, pentobarbital, perphenazine, phenobarbital, phenylbutazone, phtomenadione, pirenzepine, polythiazide, prazosine, prednisolone, ester thereof, prednisone, ester thereof, probenecid, propranolol, propylthiouracil, rescinnamine, reserpine, secbutabarbital, secobarbital, spironolactone, sulfasalazine, sulfonamide, thioridazine, triamcinolon, ester thereof, triamteren, trichlormethiazide, trifluoperazine, trifluopromazine, tuberculostatic, verapamil, virustacic, zytostatic, bromocriptine, bromopride, carbidopa, carbocromen, quinine, chlorprothixene, cimetidine, clofibrat, cyclizine, desipramine, disulfiram, domperidone, doxepine, fenbufen, flufenamine acid, flunarizine, gemfibrocil, haloperidol, ketoprofen, labetalol, lorazepam, mefenamine acid, melperone, metoclopramide, nortriptyline, noscapine, oxprenolol, oxymetholone, pentazocine, pethidine, stanozolol, sulindac, sulpiride, tiotixen, aciclovir, alclofenac, non steroidal anti inflammatory drugs, alprenolol, apomorphine, cyclosporine, spasmolytica, anti anginosa, diuretics, anti emetics. anti diareica, hypnotica, sedativa, anxiaolytica, neurleptica, anthistaminica, cimetidine, ranitidine, famotidine, benzodiazepines, isoprenaline, salbutamol, efedrine, acetylcycteine, carbocisteine, pseudoefedrine, xylometazoline, tramazoline, antheminthica, anti mallaria.

EXAMPLE 11

An emulsion has been prepared as in example 6, but by using 70 g water, 8 g isomalt, 20 g soya-bean oil, 2.5 g spironolactone, 2 g methylcellulose and 0.5 g aspartame.

Tablets have been prepared in the same manner as disclosed in Example 6. The tablets contained 62 mg Isomalt, 160 g Soya-bean, 20 mg spironolactone, 16 mg methylcellulose and 4 mg aspartame.

EXAMPLES 12 AND 13

The following tables give the composition of the solution prepared and the dry solid content of the tablets prepared:

| Solution composition | | Tablet composition (mg) |
|---|---|---|
| Isomalt | 4 g | 160 |
| Xanthan gum | 0.1 g | 4 |
| PEG 6000 | 0.2 g | 8 |
| Hydrochlorothiazide | 1.25 g | 50 |
| Ascorbic acid | 0.05 g | 2 |
| Sodium saccharinate | 0.01 g | 0.4 |
| Deionized water | to 20 ml | |
| Maltodextrin DE 22 | 4 g | 160 |
| Xanthan gum | 0.1 g | 4 |
| Griseofulvin | 1.25 g | 50 |
| Ascorbic acid | 0.05 g | 2 |
| Sodium cyclamate | 0.01 g | 0.4 |
| Deionized water | to 20 ml | |

What we claim is:

1. Freeze-dried disintegrating tablets, said tablets containing at least a therapeutic agent, a matrix forming agent and a binding agent, in which the tablets contain more than 20% by weight of a matrix forming agent selected from the group consisting of maltodextrins having a DE value between 12 and 40, isomalt and mixtures thereof, the weight ratio between said matrix forming agent and the binding agent being comprised between 2:1 and 50:1, in which said matrix forming agent and the binding agent are present in the tablets in an amount for ensuring a strength of the tablets of at least 1.5N and a disintegration time of the tablets between 10 and 120 seconds, said strength being the maximal force recorded when penetrating at a speed of 0.1 mm/second a cone probe over a depth of 1 mm in a tablet.

2. The tablets of claim 1, in which the binding agent is selected from the group consisting of water soluble thickening agents.

3. The tablets of claim 1, in which the binding agent is selected from the group consisting of Xanthan gum, methylcellulose, hydroxypropylmethylcellulose, hydroxyethylcellulose and mixtures thereof.

4. The tablets of claim 1, said tablets further containing at least a cosolvent for the therapeutic agent.

5. The tablets of claim 4, said tablets containing from 0.1% to 5% by weight of the co-solvent for the therapeutic agent.

6. The tablets of claim 4, in which the co-solvent is selected from the group consisting of a polyethyleneglycol with a molecular weight lower than 10,000, glycerol. propyleneglycol, and mixtures thereof.

7. The tablets of claim 1, said tablets further containing at least a surfactant.

8. The tablets of claim 7, in which the surfactant is selected from the group consisting of a polysorbate, a lecithin, a polyethoxylated castor oil, N-octenylsuccinate starch, a sucroester, and mixtures thereof.

9. The tablets of claim 1, said tablets further containing an oil.

10. The tablets of claim 9, in which the oil is selected from the group consisting of medium chain triglycerides, soyabean oil, cotton oil, sesame oil, peanut oil, and mixtures thereof.

11. The tablets of claim 1, in which the binding agent is selected from the group consisting of Xanthan gum, cellulose derivatives, and mixtures thereof.

12. The tablets of claim 1, in which said matrix forming agent and the binding agent are present in the tablets in respective amounts for ensuring a porosity of the tablets formed by pores having a mean pore diameter between 10 $\mu$m and 15 $\mu$m.

13. The tablets of claim 1, said tablets further containing an additive selected from the group consisting of a sweetening agent, a carboxylic acid, citric acid, ascorbic acid, and mixtures thereof.

14. The tablets of claim 1, in which the tablets have the form of a substantially round lozenge with a diameter between 5 and 15 mm.

15. The method for the preparation of a freeze-dried disintegrating tablet containing at least a therapeutic agent, a matrix forming agent and a binding agent, in which a liquid medium containing at least:

(a) a compound which is liquid at a temperature higher than 0° C., which freezes at a temperature lower than 0° C., and which is sublimed at temperature lower than 0° C. and at a pressure lower than $10^2$ Pa;

(b) a therapeutic active agent;

(c) a matrix forming agent soluble in the said compound; and (d) a binding agent;

is prepared, frozen and dried at a pressure lower than 100 Pa, in which the liquid medium contains 10 to 200 grams/liter of a matrix forming agent selected from the group consisting of maltodextrins having a DE value between 12 to 40, isomalt and mixtures thereof, the weight ratio between said matrix forming agent and the binding agent being comprised between 2:1 and 50:1, in which said matrix forming agent and the binding agent are present in the liquid medium in an amount for ensuring, after freeze-drying of the liquid medium, the preparation of tablets having a strength of at least 1.5N and a disintegration time between 30 and 120 seconds, said strength being the maximal force recorded when penetrating, at a speed of 0.1 mm/second, a cone probe over a depth of 1 mm in said tablet.

16. The method of claim 15, in which the liquid medium prepared is selected from the group consisting of solutions in which at least the matrix forming agent and the binding agent are dissolved, oil emulsions in which the matrix forming agent is dissolved and suspensions of the therapeutic agent in which at least the matrix forming agent is dissolved.

17. The method of claim 15, in which the liquid medium is dried in at least two stages, a first drying stage being carried out at a temperature lower than the freezing temperature of the liquid medium at a pressure lower than $10^2$ Pa, and a second stage being carried out at a temperature higher than the freezing temperature of the liquid medium at a pressure lower than $10^2$ Pa.

18. The method of claim 15, in which the liquid medium contains from 1 to 30 g/liter of a binding agent selected from the group consisting of water soluble thickening agents.

19. The method of claim 18, in which the binding agent is selected from the group consisting of Xanthan gum, methylcellulose, hydroxypropylmethylcellulose, hydroxyethylcellulose and mixtures thereof.

20. The method of claim 15, in which the liquid medium contains at least a solvent for the therapeutic agent.

21. The method of claim 20, in which the liquid medium further contains at least a co-solvent for the therapeutic agent, said co-solvent having a boiling point higher than a temperature of the liquid medium during drying at said pressure lower than $10^2$ Pa.

22. The method of claim 15, in which the liquid medium further contains at least a surfactant.

23. The method of claim 22, in which the surfactant is selected from the group consisting of a polysorbate, a lecithin, a polyethoxylated castor oil, N-octenylsuccinate starch, a sucroester, and mixtures thereof.

24. The method of claim 15, in which the liquid medium contains an oil.

25. The method of claim 24, in which the oil is selected from the group consisting of medium chain triglycerides, soya-bean oil, cotton oil, sesame oil, peanut oil, and mixtures thereof.

26. The method of claim 15, in which the binding agent is selected from the group consisting of Xanthan gum, cellulose derivatives, and mixtures thereof.

27. The method of claim 15, in which said matrix forming agent and the weight ratio between said matrix forming agent and the binding agent are present in the liquid medium in an amount for ensuring a porosity of the tablets formed by pores having a mean pore diameter between 10 $\mu$m and 15 $\mu$m.

28. The method of claim 15, in which the liquid medium further contains an additive selected from the group consisting of sweetening agents, carboxylic acid, citric acid, ascorbic acid, EDTA, sulfites, bisulfites, and mixtures thereof.

29. The method of claim 15, in which the liquid medium before being frozen is dispensed into substantially round blisters with a diameter between 5 and 15 mm.

* * * * *